United States Patent [19]
Brient et al.

[11] Patent Number: 5,146,010
[45] Date of Patent: Sep. 8, 1992

[54] PYROLYSIS OF NATURALLY OCCURRING CRESYLIC ACID MIXTURES

[75] Inventors: James A. Brient, Missouri City; Marvin H. Strunk, Jr., Houston, both of Tex.

[73] Assignee: Merichem Company, Houston, Tex.

[21] Appl. No.: 743,077

[22] Filed: Aug. 9, 1991

[51] Int. Cl.$^5$ .................. C07C 37/68; C07C 41/34; C07C 39/07
[52] U.S. Cl. .............................. 568/761; 568/650; 568/651; 568/652; 568/653; 568/749; 568/751
[58] Field of Search .............. 568/761, 751, 749, 806, 568/650, 651, 652, 653

[56] References Cited

U.S. PATENT DOCUMENTS

| | | | |
|---|---|---|---|
| 3,375,283 | 3/1968 | Goheen et al. | 568/653 |
| 4,208,350 | 6/1980 | Hearon et al. | 568/653 |
| 4,420,642 | 12/1983 | Franko-Filipasic et al. | 568/652 |
| 4,900,873 | 2/1990 | Kakemoto et al. | 568/761 |

FOREIGN PATENT DOCUMENTS

| | | | |
|---|---|---|---|
| 0204474 | 11/1983 | Fed. Rep. of Germany | 568/653 |
| 1235860 | 6/1986 | U.S.S.R. | 568/761 |

OTHER PUBLICATIONS

Lawson, J. R. and M. T. Klein, "Influence of Water on Guaiacol Pyrolysis", Dept. of Chemical Engineering, University of Delaware, 1985.
Ceylan, R. and J. B-son Bredenberg, "Hydrogenolysis and hydrocracking of the carbon-oxygen bond. 2. Thermal cleavage of the carbon-oxygen bond in guaiacol", Dept. of Chemistry, Helsinki University of Technology, rev. Dec. 3, 1981.
Vouri, A. and J. B-son Bredenberg, "Hydrogenolysis and Hydrocracking of the Carbon-Oxygen Bond", Dept. of Chemistry, Helsinki University of Technology, 1984.
Bredenberg, J. and Ramazan Ceylan, "Hydrogenoloysis and hydrocracking of the carbon-oxygen bond. 3. Thermolysis in tetralin of substituted anisols", Dept. of Chemistry, Helsinki University of Technology, rev. Sept. 15, 1982.
Vouri, A., "Pyrolysis studies of some simple coal related aromatic methyl ethers", Dept. of Chemistry, Helsinki University of Technology, rev. Apr. 23, 1986.
Zhou, P. and Billy L. Crynes, "Thermolytic Reactions of o-Ethylphenol", School of Chemical Engineering, Oklahoma State University.
Journal of Organic Chemistry, vol. 36, No. 5 (1971) pp. 721-723.

Primary Examiner—Werren B. Lone
Attorney, Agent, or Firm—Kirk & Lindsay

[57] ABSTRACT

A process for removing guaiacols from naturally-occurring cresylic acid mixtures by pyrolysis is described.

8 Claims, 1 Drawing Sheet

PYROLYSIS OF NATURALLY OCCURRING CRESYLIC ACID MIXTURES

FIELD OF THE INVENTION

This invention relates to a process for removing alkoxyaromatic impurities, particularly guaiacols, from naturally occurring cresylic acid feeds by vapor phase pyrolysis.

BACKGROUND OF THE INVENTION

Cresylic acid is an important commercial product widely used in the manufacture of chemical, agrichemical, pharmaceutical and industrial intermediate products. The lowest molecular weight member of the cresylic acid family—phenol—is produced synthetically in very large quantities. The three cresols also are produced synthetically, but in much smaller quantities. The di-methyl phenols (xylenols) and other alkylated phenols are not commercially synthesized to any appreciable extent. Therefore, recovery from natural sources such as partially refined petroleum and coal via cooking, gasification, and liquefaction provides the majority of cresylic acid used in industry today. Cresylic acids recovered from these sources are heavily contaminated with aromatic organic compounds including hydrocarbons as well as those containing hetero-atoms such as nitrogen, sulfur and oxygen. Methoxy substituted phenols comprise a particularly troublesome group derived from some low grade coals such as brown coal or lignite. Guaiacol—methoxy phenol—boils near the boiling points of meta- and para-cresol and methyl guaiacols—methoxy cresols—boil in the range of the xylenols. Therefore, the guaiacol cannot be separated from the cresylic acid fractions by conventional distillation. To be useful, the various isomers of cresylic acid must be separated from the other impurities and often from each other, and therein lies the problem because, heretofore there has been no simple process for physically separating guaiacols from cresylic acid. Therefore, the guaiacol must be destroyed in the presence of the cresylic acid which also presents a problem of cresylic acid yield loss. The crude cresylic acid mixture obtained from lignite contains larger amounts of guaiacol than the mixture obtained from coal, up to almost 4% by weight, or even more. Heretofore, such destruction has been accomplished only with difficulty and the resultant loss of cresylic acid yield to byproducts, most of them unwanted heavies and coke.

Considerable academic effort has been reported relating to removal of methoxy compounds or the demethylation of phenols. This work is reported in articles, such as Lawson, J. and M. Klein, *Influence of Water on Guaiacol Pyrolysis*, Ind. Eng. Chem. Fundam., 24: 203, 1985; Ceylan, R. and J. Bredenberg, "Hydrogenolysis and Hydrocracking of the Carbon-Oxygen Bond. 2. Thermal Cleavage of the Carbon-Oxygen Bond in Guaiacol," *Fuel*, 61:377, 1982; and Vuori, A. and J. Bredenberg, "Hydrogenolysis and Hydrocracking of the Carbon-Oxygen Bond. 4. Thermal and Catalytic Hydrogenolysis of 4-Propylguaiacol," *Holzforschung*, 38:133, 1984.

The Lawson article discussed the pyrolysis at 383° C. of guaiacol, neat and in the presence of water to study the effect of the presence of water on char and byproducts formation during the pyrolysis. The byproducts produced were investigated, verifying information found in the Ceylan and Vuori articles cited above. Batch reactors, 98% pure guaiacol and isothermal conditions were employed. The reactor was removed from heat after reaction times of from 15 to 90 minutes and cooled with water and the products analyzed. The presence of water decreased the formation of coke but also disclosed increased catechol yield with o-cresol yield being decreased with the increased amount of added water. The article confirms that when fission occurs, it is the weaker phenoxy-methyl bond which breaks, resulting in phenol and methane products. However, it was found by the inventors of this invention that the pyrolysis at the temperatures disclosed in the articles does not reduce the guaiacol composition of a crude cresylic acid feed stream derived from coal, much less lignite. Such academic discussion therefore, is no help to develop a process for the removal of guaiacol from such feedstreams to recover the cresylic acid. Prior art does point out the problem of byproduct creation during reaction of such heterogeneous streams but offers no real solution to the problem.

SUMMARY OF THE INVENTION

Figure 1:
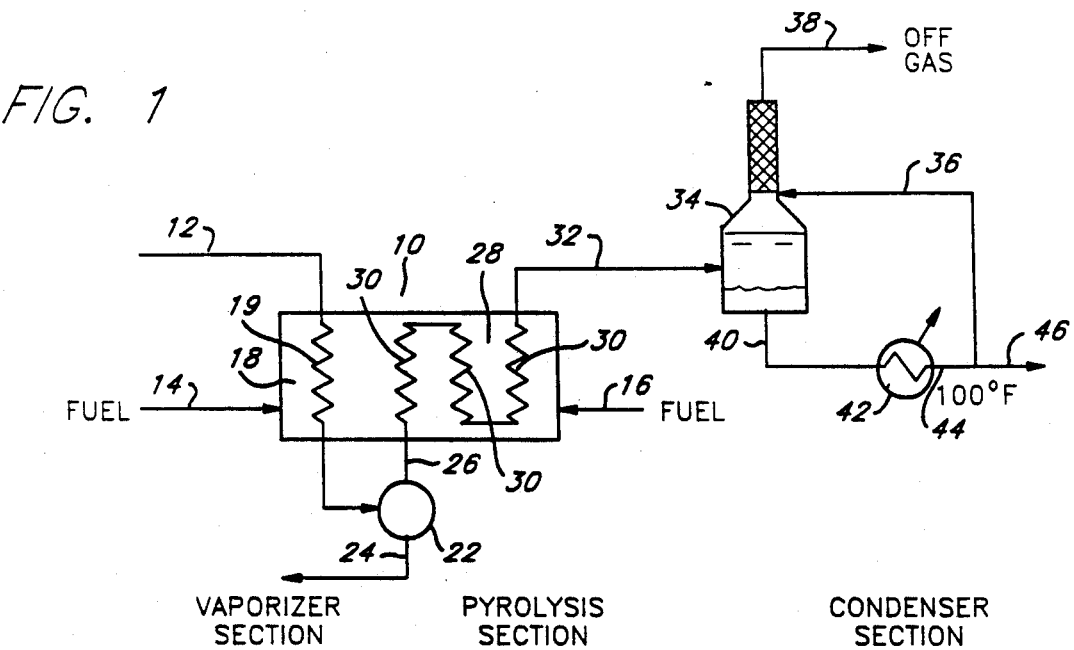
FIG. 1 is a schematic flow diagram of a preferred embodiment of this invention with common process components such as pumps valves and instrumentation not shown.

This invention involves substantially complete removal of guaiacol from cresylic acid feed streams, with very low yield losses of cresylic acid using a vapor phase pyrolysis process. Naturally occurring cresylic acid streams recovered from coal, coal tar, natural gas or lignite containing up to about 4% guaiacol are vaporized and, in the practice of this invention, passed through a hot tube reactor at least about 450° C. at pyrolysis conditions, preferably at 500° to 600° C. to demethylate the guaiacol and leave the cresols virtually untouched. Process variables such as temperature, flow rate, pressure, and addition of water to the feed are controlled to improve guaiacol reduction, byproduct formation, and coke and gas formation. Variations in the cresylic acid feed matrix (m-, p-cresol, coal based cresylic acid, and depitched, dephenolized cresylic acid, for example) and guaiacol levels in feed also affect performance of the process.

DETAILED DESCRIPTION OF THE INVENTION

This invention is the vapor phase pyrolysis of naturally occurring cresylic acid mixtures recovered from the pitch residual in removal of liquids from coal, coal tars, lignite or natural gas condensates. These naturally occurring cresylic acid-containing mixtures include several methoxyaromatic impurities, particularly guaiacol, which is often present in amounts up to about 4% and sometimes about 6% by weight, where the materials comes from a lignite source and about 2% where the cresylic acid mixture which forms the feed for the practice of this invention is recovered from coal, or a coal tar. The process of this invention would successfully operate to remove even greater amounts of guaiacols in naturally occurring feeds and should not be considered limited to one containing 4% by weight.

The presence of such methoxyaromatic impurities significantly reduces the commercial value of the cresylic acid as a raw material for high quality plastics and resins. The crude feed is usually treated to remove residual pitch and distilled to remove phenols and light low-boiling hydrocarbons; i.e., those materials which have boiling points below or near that of the phenol being removed. In the practice of this invention, the feed is vaporized in any number of ways well-known to those skilled in the art and fed into a tubular reactor which is externally heated, much like steam in a boiler tube or in thermal cracking unit operations, such as in use for thermal cracking of naptha to obtain ethylene in a boiler. The material preferably used for the tubular reactor would be steel, preferably stainless steel, such that the vapors flow smoothly through the zone being heated. The tubular reactor may optionally be packed with an inert packing such as beryl saddles, steel tower packings and the like to aid in uniform heat distribution. The tubular reactors may be oriented with the longitudinal axis either horizontal or vertical, as long as the heating is uniform.

The reactor is operated at a temperature of at least about 450° C. as long as the other conditions, pressure and throughput, result in pyrolysis conditions, satisfactorily at temperatures from about 475°-625° C., preferably from about 500° C. to about 600° C. and most preferably from about 530° C. to about 580° C. Temperature and flow rate are the two main process variables effecting guaiacol destruction and subsequent removal. Operation at about 550° C. and a liquid hourly space velocity (LHSV) of 0.6-1.4 $hr^{-1}$, particularly 1 $hr^{-1}$ were discovered to be the optimal conditions for pyrolysis of guaiacol in dephenolized cresylic acid from a lignite source. A minimum temperature of about 530° C. was found necessary to reduce guaiacol to non-detectable levels (<10 to 20 ppm) at LHSV 0.6 $hr^{-1}$. As the temperature drops below 450° C., the amount of guaiacol increases with about 2% remaining in the reaction product after the reaction at about 400° C., therefore making it very unattractive and almost futile to use such low temperature. Other factors determine satisfactory pyrolysis conditions and can be set using economic and commercially satisfactory conditions. High temperature may be used but the pressure and rate of throughput must correspondingly increase.

The maximum flow rate which consistently gave substantially complete guaiacol removal at 530°-550° C. and atmospheric pressure was at a LHSV 0.6 $hr^{-1}$. Table A shows that unreacted guaiacol in meta, para-cresol treated at 530° C. increased from non-detectable to <0.02% when space velocity was increased from 0.6 to 1.2 $hr^{-1}$. Increasing space velocity to 1.7 $hr^{-1}$ further increased guaiacol in the product to 0.10%. Complete removal of guaiacol at LHSV 1.7 $hr^{-1}$ was only achieved when the reactor temperature was raised to 600° C. However, the higher flow rates allowed by high temperature operation came at the expense of increased coke and gas production. Formation of coke increased from 0.1% to 0.4% and gas production more than doubled when the reaction temperature was increased from 540° to 600° C. (Table A). Light neutral byproducts doubled in quantity, phenolic byproducts increased by 25%, and heavy byproducts ($C_1$-$C_2$ dibenzofurans) more than doubled.

TABLE A

Byproducts from Guaiacol Pyrolysis at 540° C. 5/28 and LHSV 0.6 $hr^{-1}$ (Weight %)

| Source → | m,p-Cresol | | Coal Based | | Lignite Based | |
|---|---|---|---|---|---|---|
| Component | Feed | Product | Feed | Product | Feed | Product |
| Lights[1] | tr | 0.3 | — | 0.3 | 0.7 | 1.0 |
| Phenol | — | 0.6 | 32.5 | 34.0 | 24.5 | 26.3 |
| o-Cresol | 0.1 | 0.7 | 14.8 | 15.2 | 17.4 | 18.0 |
| m,p-Cresol | 95.8 | 97.0 | 29.5 | 29.4 | 46.1 | 46.4 |
| 2,4/2,5-Xylenol | tr | 0.2 | 5.2 | 5.4 | 2.9 | 2.8 |
| Other CA | 0.1 | 0.2 | 12.4 | 12.6 | 4.5 | 4.4 |
| Heavies/Alks | — | 0.1 | 3.6 | 2.5 | 0.8 | 1.1 |
| Guaiacol | 4.0 | — | 2.0 | — | 3.9 | — |
| Catechols | — | 0.9 | — | 0.8 | — | 1.1 |

[1]Neutral oils and nitrogen bases b.p. lower than for phenol.

The pressure range for operating the pyrolsis of this process is from about atmospheric pressure to about four atmospheres, preferably about atmospheric pressure for cost considerations and product recovery. Operation of the pyrolysis process under slight pressure of from about 4 to about 12 psig had beneficial effects on guaiacol removal. Operating under pressure significantly increases guaiacol removal while having little or no effect on gas production but would result in greater coke formation. This was the expected result since the residence time was increased by operating under pressure, (i.e., doubling the system pressure while maintaining constant mass flow rate would decrease the volumetric flow rate by one-half) allowing higher flow rates or lower operating temperatures to be used while achieving guaiacol removal similar to that obtained at atmospheric pressure. Equipment sizing in a commercial process might also be reduced by operating under pressure.

Cresylic acid composition influenced guaiacol removal efficiency and byproducts. Byproduct formation was much more evident when using meta, para-cresol mixture as a feed than when full range acid feed was processed. Complete removal of guaiacol from dephenolized lignite based cresylic acid (4% guaiacol) was slightly more difficult to achieve than from meta, para-cresol mixtures spiked with guaiacol for test purposes or coal based feed. meta, para-Cresol treated at 530° C. and LHSV 0.6 $hr^{-1}$ had no detectable guaiacol remaining, while the lignite based feed treated under similar conditions contained 150 ppm guaiacol. Similar results were found when temperatures and space velocities were varied, as shown in Table B.

TABLE B

Effect of Feed, Temperature, and Flow Rate on Guaiacol Removal

| Feed Matrix | Guaiacol % | Temp., °C. | Guaiacol in Product, % | | |
|---|---|---|---|---|---|
| | | | LHSV 0.6 $hr^{-1}$ | LHSV 1.2 $hr^{-1}$ | LHSV 1.7 $hr^{-1}$ |
| m,p-Cresol | 4 | 480 | 0.441 | NA[1] | NA |
| | | 500 | 0.051 | NA | NA |
| | | 530 | nil[2] | 0.018 | 0.101 |
| | | 550 | nil | nil | 0.006 |
| | | 600 | nil | nil | nil |
| Coal based | 2 | 550 | nil | NA | NA |
| Lignite based | 3.9 | 530 | 0.015 | 0.183 | NA |
| | | 550 | 0.001 | 0.008 | NA |
| Lignite based* | 3.9 | 550 | 0.009 | 0.031 | NA |
| | | 600 | nil | nil | nil |

[1]NA = Not Analyzed
[2]nil = less than minimum detectable limit (<10-20 ppm)
*5% by weight $H_2O$ The quantity of off-gases and coke produced was proportional to the concentration of guaiacol in the feed. Comparing coal-based feed with lignite-based feed, doubling the guaiacol content in the feed more than doubled coke formation. Although the total quantity of off-gases was also doubled, gas formation per pound of guaiacol treated was the same for both feeds. Less gas was formed per pound of guaiacol when the source was m,p-cresol than from a full range acid feed. A slight quantity of coke and gas is produced from coal-based feed containing no guaiacol under pyrolysis conditions confirmed that byproduct gases are due to guaiacol cleavage rather than cresylic acid decomposition. Gas volume increased by an order of magnitude when coal-based feed containing 2% guaiacol was treated, and coke increased from none detectable to ~0.1% of the feed as shown in Table C.

TABLE C

| Coke and Gas Formation From Guaiacol Pyrolysis | | | | |
|---|---|---|---|---|
| Feed Matrix | Guaiacol, % | Temp., °C. | Coke, % of Feed | Gas, cu ft/lb. guaiacol |
| Coal | 0 | 550 | 0 | — |
| Coal | 2 | 540 | ~0.1 | 2.64 |
| Lignite | ~4 | 540 | ~0.3 | 2.63 |
| m,p-cresol | 4 | 540 | ~0.1 | 1.93 |
| m,p-cresol | 4 | 600 | ~0.4 | 4.76 |

Water may be present in the cresylic acid feed stream as it is introduced into the reactor or added to the cresylic acid feed stream to inhibit coke formation even though its presence may inhibit guaiacol conversion slightly. Within the scope of the practice of this invention, 3% by weight or more of water may be present with the ultimate amount being determined by economic and commercial considerations with the preferred range from about 5 wt % to about 12 wt %.

Having described the various parameters of operation of the process of the invention, turning now to FIG. 1, an embodiment of the preferred practice of the invention is described. The feed enters a furnace 10 through a crude feed stream 12. In this embodiment, the furnace 10 is fired with a fuel, such as, for example, natural gas, entering in through lines 14 and 16 to burners (not shown). While any number of fuel points are commonly used, two are shown here for illustration, the fuel entering through line 14 warming a vaporization zone 18 where the crude feed entering through line 12 is vaporized. The vaporized crude cresylic acid stream containing guaiacol passes through the vaporization zone 18 through tubes 19 and exits through line 20 and proceeds to a knock-out drum 22 where the vaporized feed is separated from a residue which exits the knock-out drum 22 through a line 24 for disposal or use. The vapors exit the knock-out drum 22 through line 26 and reenter the furnace 10 into the pyrolysis zone 28 where it passes through a tubular reactor 30 in the pyrolysis zone 28. It is here, operating at the pyrolysis conditions previously discussed, that the guaiacol and other methoxyaromatics are converted to pyrolysis reaction, or degradation, products. The pyrolyzed vapor stream leaves the pyrolysis zone 28 through line 32 where it enters a quench condenser 34. There, the pyrolysis products are contacted with a quench stream, preferably cooled condensed cresylic acid entering the quench condenser 34 through line 36. Prompt quenching serves the primary purposes of halting all reactions occurring in the pyrolysis and liquefying the cresylic acid. In the practice of this invention, surprisingly small amounts of byproduct are formed and very little cresylic yield is lost. Non-condensible gases such as, for example, carbon monoxide, methane and nitrogen leave the quench condenser 34 through line 38 for use or environmentally proper disposal with the quenched cresylic acid product exiting the quench condenser 34 through a bottoms line 40 as a liquid and thence, to a condenser 42, preferably cooled with water on the shell side, where the product stream is further cooled to from about 55° to about 70° C. This temperature is not critical but resort to this modest range has been found to work well. This cooled cresylic acid product leaves the heat exchanger 42 through line 44 substantially free of guaiacol impurities, and thence to line 36 where a portion of it is recycled to the quench condenser 34. The amount of cooled cresylic acid mixture to be recycled may be readily calculated using the thermodynamic properties of the pyrolysis product stream readily available to the skilled engineer. Usually from about one-fourth to about three-fourths of the stream exiting the heat exchanger 42 will be recycled to the condenser 34. Preferably, from about 40% to 60% will be recycled, depending upon the thermodynamics of the system. A treated product of cresylic acid, substantially free of the troublesome guaiacol, is bled from line 44 through line 46 and is carried thence to a storage tank for further processing for sale or use.

The quench condenser 34 is operated at substantially atmospheric pressure or at sub-atmospheric pressure to improve the removal of the off-gases and non-condensible vapors. The quench is operated for the dual purpose to halt the pyrolysis reaction to prevent the formation of byproducts and reduction of cresylic acid yield which would otherwise be lost through the formation of a heavies stream. The treated product exiting through line 46 then may be more refined by flash distillation, not shown. Recovery of treated flash distillation products confirmed that significant formation of high boiling materials did not occur during the pyrolysis process of this invention and that the vacuum flash distillation of the pyrolysis products of the two samples of coal based feed containing 0 and 2% guaiacol gave distillate recovery of 99.99+% and 99.1%, respectively. The flash distillation normally occurred at about 100 mm mercury.

Figure 2:
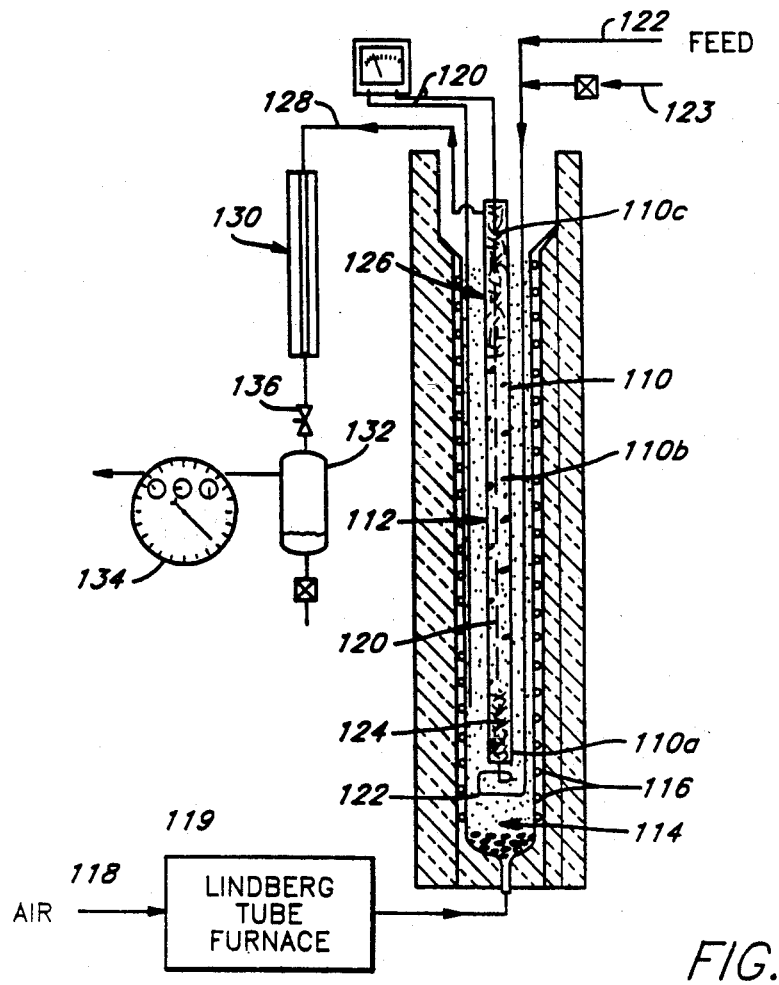
FIG. 2 is a flow diagram, partially in schematic form, showing the test equipment used to perform the examples of this invention.

The above-described invention will be more specifically exemplified by the following discussion of the test equipment shown in FIG. 2 and the process by which the process of the invention was developed. It must be recognized that the equipment, steps of the process and sequence in which these steps are performed may be varied or modified without departing from the scope and spirit of the invention herein described and exemplified which follows.

DESCRIPTION OF EQUIPMENT AND TEST PROCEDURE

Vapor phase pyrolysis of guaiacol tests were run in a ½" internal diameter×28" long 316 stainless steel pipe reactor tube 110, shown schematically in FIG. 2. The pipe was packed with inert materials 112 (stainless steel packing, glass spheres, or MgO pellets) to paid heat transfer. A fluidized sand bath 114, held by an outer pipe 115 and heated by two 1500 watt nichrome heaters 116, in turn heated the reactor 110 and provided even temperature control. Air to fluidize the sand bath entered through line 118 and was preheated to 500°–600°

C. in a 1"×12" pipe, packed with alloy 20 skived fibers, placed in a Lindberg tube furnace 119. Thermocouples 120 measured the sand temperature and reactor internal temperature. The feed stream 122 joined by an optional air or nitrogen diluent stream 123 were pumped into the reactor 110 with a MPL Series 2 micropump (not shown) at 100-300 ml/hour to perform the tests which are described later. The feed entering line 122 passed through the heated sand 114 where the feed was vaporized. The feed entered the tubular reactor 110 at the bottom 110a, passed through stainless steel column packing 124 and upwardly through the reactor tube 110 in the pyrolysis zone 110b. The top of the tubular reactor 110c was packed with alloy 20 (Carpenter Steel Co) fiber 126. The pyrolyzed product exits the top of the reactor 110c through line 128 and is condensed in condenser 130. Vaporized product from the reactor 110 was cooled in the condenser 130 and collected for analysis in product receiver 132. Off-gases were measured in some runs with a wet test meter 134 with 0.001 cubic feet divisions. Operation of the lab scale unit was performed as described above, by pumping the cresylic acid/guaiacol feed through a rotameter into the preheater/reaction zone within the heated sand bath 114, followed by cooling in the condenser 130 and collecting the treated product in the receiver 132. Runs made under pressure used a variable set point pressure relief valve 136 to maintain about ~30 psig on the system. Cresylic acid isomer distribution as well as neutral oil content were measured by GLC following well known procedures. Residue was determined on selected composite samples by flashing at 100 mm Hg until the overhead temperature began to drop (generally ~165° C.). Residue remaining in the flask was weighed and reported as a percentage of the cresylics charged. Coke formation was calculated by weighing the reactor tube before and after the run, with any residual cresylic acid having been removed by a steam purge of the system. While the above described methods and apparatus were used to conduct the tests described in Examples I through IV which follow any comparable test procedures and instruments, know in the art are acceptable.

EXAMPLE I

A mixture of m, p-cresol containing 4% guaiacol was prepared and passed through a vaporizer assembly and tubular reactor packed with an inert material for heat transfer, as described above and shown in FIG. 2. The reactor in a fluidized sand bath was heated to 500°-600° C. and operated at atmospheric pressure. The cresylic acid flow corresponded to a LHSV of 0.6-1.7 hr$^{-1}$. The treated product exited the reactor and was passed through a condenser and collected for analysis. The following table summarizes run data at various temperature and space velocities.

| Temp., °C. | Guaiacol in Product: | | | Coke, % of Feed | Gases, cu ft/ lb Guaiacol |
|---|---|---|---|---|---|
| | 0.6 hr$^{-1}$ | 1.2 hr$^{-1}$ | 1.7 hr$^{-1}$ | | |
| 500 | 0.44 | NA | NA* | NA | NA |
| 530 | 0.05 | NA | NA | ~0.1 | 1.9 |
| 550 | n.d.** | 0.02 | 0.10 | NA | NA |
| 600 | n.d. | n.d. | n.d. | ~0.4 | 4.8 |

*Not analyzed
**Non-detected

Byproducts from the reactor included 1.7% other phenolics, 0.3% lights, 0.1% heavies, and 0.9% catechol.

EXAMPLE II

Coal-based cresylic acid containing ~4% guaiacol (added to form mixture) was passed through the reactor in the same way as in Example I at 530° C. to give 0.02% unreacted guaiacol at 0.6 hr$^{-1}$ LHSV and 0.18% guaiacol at 1.2 hr$^{-1}$. Treating the coal-based cresylic acid feed at 550° C. reduced guaiacol to trace levels at 0.6 hr$^{-1}$ and to <0.01% at 1.2 hr$^{-1}$.

EXAMPLE III

Using the test equipment and procedure described above, a number of runs were made to determine optimum conditions to completely pyrolyze guaiacol. Factors that affect coke formation were determined to investigate conditions where coke was not formed. Three types of runs were made:

1. Stainless steel reactor with guaiacol-spiked m-cresol feed.
2. Stainless steel reactor with depitched, dephenolized lignite-based cresylic acid feed.
3. Quartz reactor arranged as in FIG. 2 with guaiacol-spiked m-cresol feed.

The quartz reactor configuration was similar to that of the stainless steel reactor described above. The reactor was operated at isothermal conditions to the condenser by wrapping with heat tape and using an additional temperature controller.

Guaiacol-spiked meta-cresol was used as feed in this Example, so that products of guaiacol pyrolysis could be distinguished and cresylic acid yield losses could be calculated more easily. The effects of pressure and temperature were studied. When pressure was varied, no attempt was made to keep the residence time constant by varying the flow rate. Therefore, in this Example, differences in pressure show the effects of pressure and residence time variations. The actual residence time in the reactor, assuming ideal gas behavior, was 19-20 seconds for the atmospheric pressure runs and 51-53 seconds for 25 psig runs. Pressure and temperature were varied in runs in the steel reactor. At 500°, or 470° C. and 25 psig, essentially complete guaiacol removal was observed. At 470° C. and atmospheric pressure, the guaiacol removal dropped off to 91.6%. Cresylic acid yield loss was 4-5% for these latter conditions. A summary of the pyrolysis runs are shown in Table I.

TABLE I

| Vapor Phase Removal of Guaiacol Summary | | | | | | | | | | | | | | |
|---|---|---|---|---|---|---|---|---|---|---|---|---|---|---|
| Temperature, °C. | | Pressure, psig | | | | | | Product Analysis, % | | | | Guaiacol | Meta. Cresol, Wt. % | |
| Sand Bath Air | Re- actor | Top of Con- denser | Btm. of Con- denser | Off Gas$^b$ (cc/ g Fd) | Flow Rate (ga/min) Feed Prod. | | (Gua) Feed % | Gua | Phenol | Ca- tech. | Hvies | Removal % | Feed | Product Loss |

Stainless Steel Column

TABLE I-continued

Vapor Phase Removal of Guaiacol Summary

| Temperature, °C. | | | Pressure, psig | | Off Gas[b] (cc/ g Fd) | Flow Rate (ga/min) | | (Gua) Feed % | Product Analysis, % | | | | Guaiacol Removal % | Meta. Cresol, Wt. % | | |
|---|---|---|---|---|---|---|---|---|---|---|---|---|---|---|---|---|
| Sand Bath Air | Re- actor | Top of Con- denser | Feed | Btm. of Con- denser | | Feed | Prod. | | Gua | Phenol | Ca- tech. | Hvies | | Feed | Product | Loss |
| 503 | 500 | 438 | 25 | 26 | 15.8 | 1.79 | 1.69 | 3.43 | 0.01 | 0.91 | 0.56 | 2.48 | 99.8 | 94.9 | 90.1 | 5.1 |
| 506 | 500 | 488 | 0 | 0 | 3.9 | 1.81 | 1.77 | 3.42 | 0.01 | 0.61 | 0.90 | 2.44 | 99.6 | 94.9 | 90.8 | 4.3 |
| 472 | 470 | 470 | 0 | 0 | 3.9 | 1.80 | 1.75 | 3.37 | 0.28 | 0.31 | 0.88 | 2.19 | 91.6 | 94.9 | 90.9 | 4.2 |
| 475 | 470 | 468 | 24 | 26 | 13.9 | 1.77 | 1.66 | 3.37 | 0.01 | 0.74 | 0.54 | 2.75 | 99.8 | 94.9 | 91.2 | 3.9 |
| Quartz Column | | | | | | | | | | | | | | | | |
| 501 | 500 | 499 | 0 | 0 | 3.0 | 1.78 | 1.71 | 3.37 | 0.12 | 0.41 | 0.89 | 2.03 | 96.5 | | | |

Footnotes:
[a] All runs in this table used guaiacol-spiked into meta cresol.
[b] Non condensible gas products were primarily methane and carbon monoxide.

The following conclusions can be drawn from the test results:
1. Guaiacol conversion was nearly 100% for three of the four conditions that were used: 500° C. at 0 and 25 psig and 470° C. at 24 psig. At 470° C. and atmospheric pressure, the guaiacol conversion dropped off to 91.6%.
2. The meta-cresol yield loss was essentially contant at 4–5% throughout the study. Losses were very low when pure meta-cresol, and no guaiacol, was fed to the reactor.
3. The amount of catechol produced was higher at atmospheric pressure. At 25 psig, the amount of phenol produced was higher than at atmospheric pressure.
4. The rate of formation of non-condensibles appears to be a function of pressure (and/or residence time) and is not influenced appreciably by the reactor temperature. The non-condensibles amounted to about 1% of the feed.
5. Methane and carbon monoxide were the predominant non-condensible gases.
6. The amount of heavies produced was essentially constant at 2.2–2.8% for all of the conditions investigated.

Full range lignite-based depitched cresylic acid was fed to the stainless steel reactor for two runs at 500° C. and 25 psig with results similar to those obtained with meta-cresol spiked with guaiacol. There was complete guaiacol conversion at those conditions.

Coke buildup occurred in the quartz reactor. The rate of coke formation was determined to be 0.011 wt. % of the feed.

EXAMPLE IV

These runs were performed in the equipment previously described using the same prodedures to investigate the effect of water to reduce or eliminate coke formation. Water is commonly added to pyrolysis reactors to reduce coke formation. Guaiacol in meta-cresol was pyrolyzed in two stainless steel reactors at 500° C. and atmospheric pressure and in a quartz reactor using three different water to cresylic acid ratios: 0, 0.18 and 1.0 (wt/wt). The rate of coke formation for the three cases was 0.12%, 0.07% and 0.01% (relative to feed rate), respectively. Guaiacol removal was greater than 96% for all three cases, although the reactor residence times were not kept constant because no adjustment was made for the large effect of water on vapor volume. Runs made at the high water ratio had a shorter residence time than the other two runs. Yield losses appeared to be less with water addition, although the differences in yield loss between different conditions were within experimental error. The rate of off gass and heavies formation varied slightly between the different conditions, but not significantly. Increasing amounts of water increased the relative amount of off gas and reduced the amounts of catechol, heavies and coke. The changes in off gas, catechol and heavies were relatively minor, but the changes in coke formation were dramatic. Coke formation decreased about 40% at the 0.18:1 W/C (water/cresol) ratio, from 0.12% to 0.07%, as compared to the no water case and about 90% less coke was formed at the 1:1 W/C ratio.

Water addition did not seriously reduce the reaction rate. Guaiacol conversion was greater during the runs with the 0.18:1 W/C ratio than in the runs made without any water addition. The runs made at the 1:1 ratio had about the same guaiacol conversion as the runs made without water, even though the residence time was three to four times lower with the water addition.

The addition of water to the reactor appeared to reduce the total cresylic acid and meta-cresol yield losses, although the differences were within experimental error. Under equivalent operating conditions, 500° C. and atmospheric pressure, yield losses were greater in the stainless steel column than in the quartz column, although the measurements were again within experimental error. Residence times and guaiacol conversions were slightly different between the two reactors, 19 seconds and 99.6% conversion for the stainless steel reactor and 15 seconds and 96.5% conversion for the quartz reactor.

As is seen by the disscussion above, pyrolysis is a simple, efficient method for removing guaiacol from lignite-based feed as well as the other naturally-occurring sources of cresylic acid. The advantages of the process of this invention can be achieved by adjusting operating conditions in accordance with the above-described process to achieve complete guaiacol removal, low cresylic acid yield losses and low byproduct formation. While under certain conditions coke formation results from the practice of this invention, given the discussion and examples above, many modifications of the process and conditions described may be made by those skilled in the art to achieve a wide varience of results to suit specific needs or objectives without departing from the scope of the invention described and claimed herein.

We claim:
1. A process for removing methoxyaromatic impurities from a vaporized feed stream of naturally occurring cresylic acid mixtures which comprises:

passing the vaporized feed stream through a heated tubular reactor at a temperature of at least about 450° C. at pyrolysis conditions to form a pyrolysis product stream;

quenching the pyrolysis product stream to halt by-product formation and condense cresylic acid;

removing non-condensible gaseous compounds from the quenched pyrolysis product stream; and recovering the cresylic acid from such product stream.

2. The process of claim 1 wherein the pyrolysis conditions comprise a temperature of from about 475° C. to about 625° C;

a pressure of from about atmospheric to about four atmospheres; and a hourly space velocity through the tubular reactor is from about 0.5 to about 2.0 per hour.

3. The process of claim 2 operated to maximize guaiacol removal wherein the temperature is from about 530° C. to about 580° C., the pressure is about atmospheric pressure and the linear hourly space velocity is from 0.6 to 1.4 per hour.

4. The process of claim 2 operated to maximize feed stock throughput wherein the temperature is from about 575° C. to about 600° C., the pressure is from about two to four atmospheres and the linear hourly space velocity of from about 1.7 per hour or greater.

5. The process of claim 1 operated to minimize coke formation wherein the vaporizer feed stream includes at least about 3% by weight water.

6. The process of claim 1 wherein the heated tubular reactor is made of stainless steel and packed with an inert packing material.

7. The process of claim 1 wherein the process also includes the steps of cooling the quenched pyrolysis stream and;

recycling a sufficient amount of the cooled quenched pyrolysis stream to quench the pyrolysis product stream.

8. A process for removing guaiacol from a naturally occurring cresylic acid mixture which comprises filtering the cresylic acid mixture to remove pitch;

distilling the mixture to remove phenol and impurities having low boiling points;

vaporizing the depitched, dephenolated cresylic acid mixture containing guaiacol;

passing the vaporized mixture through a tubular reactor heated to a temperature of from 530° C. to 580° C. at about atmospheric pressure at a hourly space velocity of 0.6 to 1.2 per hour to convert by pyrolysis substantially all the guaiacol to pyrolysis products leaving the cresylic acid mixture substantially free of guaiacol;

quenching the guaiacol-free cresylic acid mixture with a stream of cooled cresylic acid mixture in a quench condenser vessel to halt pyrolysis by-product formation and to condense cresylic acid;

removing a stream of non-condensed gases from the quench condenser vessel as an overhead stream and the condensed cresylic acid stream as a bottoms stream;

cooling that bottoms stream to a temperature of from 55° C. to 65° C. to form a cooled cresylic acid mixture;

recycling from one-fourth to three-fourths of the cooled cresylic acid mixture to the condenser vessel; and recovering the rest of the cresylic acid.

* * * * *